Figure 1A:
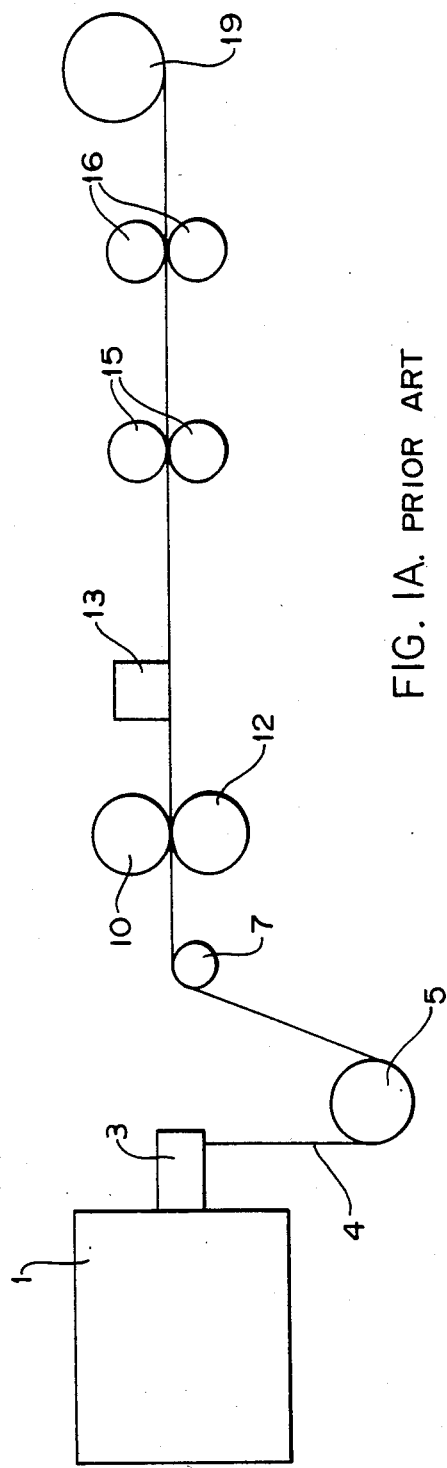

United States Patent [19]

Stallard

[11] Patent Number: 4,646,766
[45] Date of Patent: Mar. 3, 1987

[54] DENTAL TAPE

[75] Inventor: John A. Stallard, Skipton, England

[73] Assignee: Johnson & Johnson, New Brunswick, N.J.

[21] Appl. No.: 534,847

[22] Filed: Sep. 21, 1983

[30] Foreign Application Priority Data

Oct. 1, 1982 [GB] United Kingdom ............... 8228116

[51] Int. Cl.$^4$ ............................................. A61C 15/04
[52] U.S. Cl. ...................................... 132/91; 132/89;
132/92 R; 132/92 A; 132/93; 428/364
[58] Field of Search .............. 132/91, 89, 92 R, 92 A, 132/93; 428/364

[56] References Cited

U.S. PATENT DOCUMENTS

| 872,908 | 12/1907 | Cutter | 132/93 |
|---|---|---|---|
| 1,149,376 | 8/1915 | Leonard et al. | 132/93 |
| 3,863,655 | 2/1975 | Smith | 132/91 |
| 4,019,522 | 4/1977 | Elbreder | 132/91 |

FOREIGN PATENT DOCUMENTS

| 1531720 | 11/1978 | United Kingdom | 132/93 |
|---|---|---|---|
| 1531734 | 11/1978 | United Kingdom | 132/93 |
| 2012663 | 8/1979 | United Kingdom | 132/93 |
| 2034243 | 6/1980 | United Kingdom | 132/92 |
| 2128133 | 4/1984 | United Kingdom | 132/91 |

Primary Examiner—Richard J. Apley
Assistant Examiner—Gregory Beaucage
Attorney, Agent, or Firm—Steven P. Berman

[57] ABSTRACT

A dental tape is constituted by a length of incipiently fibrillatable plastics film. The tape may be made by extruding a polypropylene film in strip form onto chilled take-off rollers and then roll embossing the film by means of hardened steel rollers. After embossing, the film is oriented by means of draw rollers.

In an alternative embodiment, the tape is made by partially fibrillating a plastics film by means of a spiked roller, followed by drawing to orient the film.

The dental tape may be contained in a hand-held dispenser.

2 Claims, 3 Drawing Figures

DENTAL TAPE

This invention relates to dental floss, and in particular to dental floss in the form of tape.

Dental floss is often recommended as a means of interdental cleaning to supplement brushing; it is extremely effective in removing interdental plaque and debris. The most commonly used dental floss consists of a loosely twisted filamentous nylon thread. The loose twisting, about three turns to the inch, serves to hold the filaments of the thread together until the floss has been manoeuvred into position between the teeth. The floss is then moved up and down against the surface of the teeth to remove plaque, including sub-gingival plaque. During this movement, the floss spreads out into filaments providing an effective abrasive action on the surface of the teeth.

The floss is usually waxed in order to assist in holding the nylon filaments together during manipulation into the interdental space, for ease of handling during manufacture, and to lubricate the floss. Even unwaxed floss requires a binder to maintain cohesion of the filaments.

An alternative form of dental floss is waxed dental tape. Commercially available dental tape is a flat untwisted nylon tape. It is regarded as especially effective in removing plaque from bridge abutments and pontics.

The present invention provides a dental tape for use in the removal of plaque from teeth, said tape being constituted by a length of an incipiently fibrillatable plastics film. Preferably, the film is a polyolefine film, for example polypropylene film. Other plastics materials suitable for forming the incipiently fibrillatable film may include for example, nylon and polyesters.

The term "incipiently fibrillatable film", as used herein means a coherent film which fibrillates spontaneously on rubbing against the surface of a tooth, and includes films which have already been fibrillated and rendered temporarily stable.

The present invention also provides dental floss in the form of an incipiently fibrillatable plastics tape contained in a hand-held package from which the desired length of tape can be dispensed.

Further provided by the present invention is a process for removing unwanted deposits from the surface of teeth, comprising rubbing a length of incipiently fibrillatable plastics tape against the said surface.

Incipiently fibrillatable tape may be produced by processes already known in the synthetic textiles art, e.g. the roll embossed film (REF) process.

In general terms, the REF process comprises longitudinally embossing a polymer film (usually a polypropylene film) between hardened steel rolls. The film is usually extruded or blown, and is cooled either by water quench or chill rolls. In one form of the process, the embossing roller is heated, but to a temperature which is such that the film does not melt. The embossed film is slit to the desired width, and is then drawn to orient the polymer. This process is described, for example, in Plastics and Rubber Processing and Applications, Vol. 1, No. 4, 1981, page 327.

In an alternative form of the existing REF process, the film is embossed while still above its melting point. It will be understood that both forms of the REF process are applicable to forming incipiently fibrillatable film for use as dental tape.

Hitherto, the embossing and orientation steps of the REF process have been under conditions such as to produce either individual continuous filaments or an embossed web which can be broken down into filaments or bundles of filaments by subsequent twisting. This material is suitable for use as a substitute for coarse natural fibres such as manilla, sisal and jute in the manufacture of ropes and twines, woven tufted carpet backing, sacks and industrial fabrics. When the REF process is used to provide a dental tape according to the present invention, it is important that a lower degree of embossing is used, so that the product is a flat tape which is stable to routine handling operations, but which can be fibrillated by abrasion during flossing. In order to minimise the likelihood of the tape becoming fibrillated during manufacture, it is desirable that yarn guides of flat cross-section be used, e.g. during winding, since conventional V-shaped yarn guides bend the tape and hence may cause premature fibrillation.

As mentioned above, the embossing operation can be performed with the film above or below its melting point. When the film is above its melting point, it is usually unnecessary to heat the embossing roller. On the other hand, if the film is embossed below its melting point, the embossing roller may be heated. A suitable temperature for the embossing roller is from 80° to 100° C., e.g. 90° C. The embossing pressure will depend on the temperature of the film, and will preferably be from 30 to 50 kg/cm$^2$ e.g. 40 kg/cm$^2$ for embossing above the melting point of the film, and from 40 to 100 kg/cm$^2$, e.g. 85 kg/cm$^2$ for embossing below the melting point of the film.

The draw ratio, i.e. the extent to which the film is stretched after the embossing step, may also be varied. Generally, a draw ratio between 5:1 and 15:1 will be employed, more preferably from 7:1 to 12:1.

As an alternative to the REF process for producing dental tape according to the invention, polypropylene or other polymer films may be partially fibrillated by means of spiked rollers as will be more particularly described below.

Figure 1B:
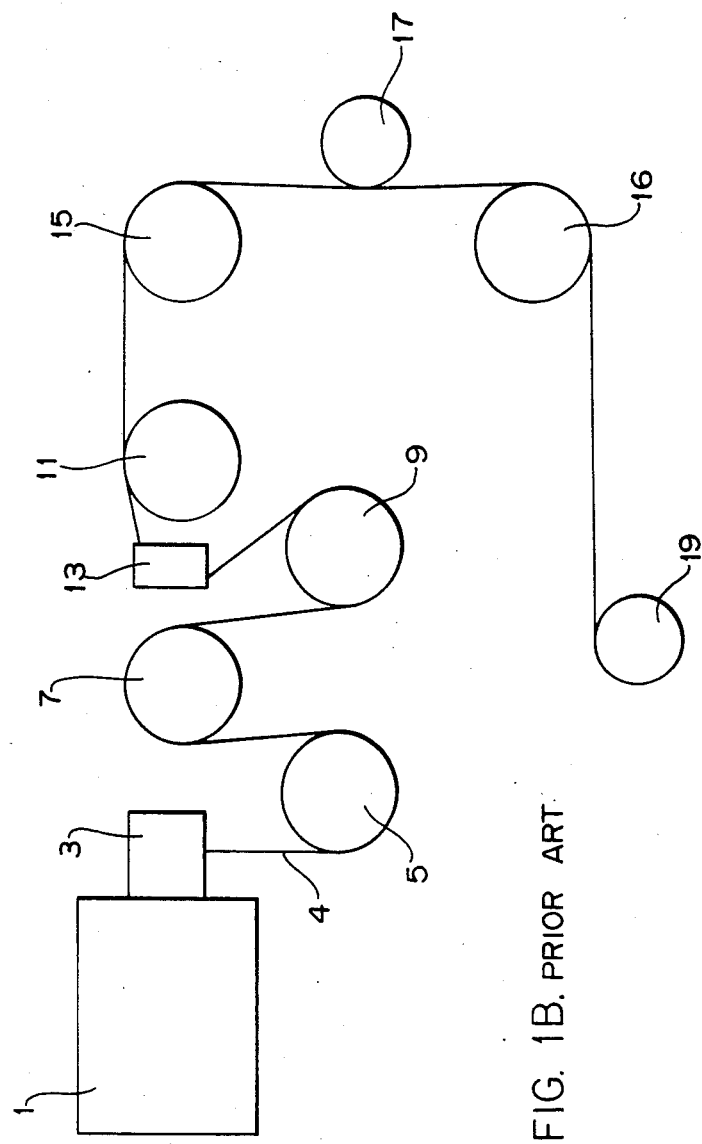
Figure 2:
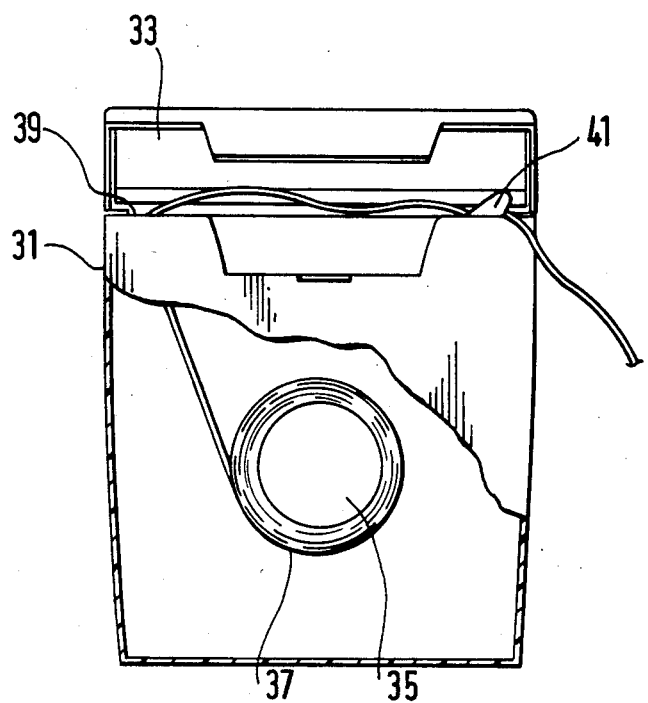

Some preferred embodiments of the present invention will now be described, by way of example, with reference to the accompanying drawings, in which:

FIG. 1A schematically represents the REF process for forming an incipiently fibrillatable film, FIG. 1B schematically represents an alternative process and apparatus, and FIG. 2 is a side elevation, partly cut away, of a dispenser suitable for dispensing dental floss in the form of incipiently fibrillatable plastics tape.

Referring to FIG. 1A, plastics material is extruded from a single screw extruder unit 1, through a sheet film casting die 3 to provide extruded drawable and orientable film 4 in strip form. The extruded film 4 passes over a chilled take-off roller 5 and a jockey roller 7 and then passes between a pair of embossing rollers, 10, 12 of hardened steel. The film should be delivered to the embossing rollers under tension, crease-free, and held to a thickness tolerance of ±5% to ensure even embossing. Roller 10 has axially spaced circumferential ribs, while roller 12 is a plain reheat roller. Roller 10 will usually have from four to ten ribs per centimeter, and more preferably from six to eight ribs per centimeter.

The embossed film then passes to a slitter unit 13 which serves to separate the embossed edge trim, and to slit the film strip into tapes of desired widths such as, for example, 1.5 mm. The slit film then passes between successive pairs of heated draw rollers 15, 16. Draw rollers 16 rotate at a higher speed than do the draw rollers 15, thus causing longitudinal orientation of the film. As is well known in the art, the draw ratio may be varied by adjustment of the relative speeds of the draw rollers 16 and 15. The embossed, slit and drawn tape is finally collected on a wind-up roller 19.

Apparatus such as that illustrated schematically in FIG. 1A is commercially available. One example of such apparatus is obtainable from Aspin Sacragrove Limited of Unit 5, Moss Lane Trading Estate, Whitefield, Manchester, England.

In FIG. 1B, plastics material is extruded from a single screw extruder unit 1', through a sheet film casting die 3', to provide extruded drawable and orientable film 4' in a manner which is analagous to that of FIG. 1A. The extruded film 4' is taken off by chilled take-off rollers 5', 7', and then passes over a pair of heated rollers 9' and 11'. A slitter unit 13' is provided downstream of roller 9' to slit the film strip 4' into tapes of desired widths, as previously described in relation to FIG. 1A. Draw roller 15' rotates at a higher speed than does the draw roller 11', thus causing longitudinal orientation of the film tape 4'.

Between rollers 15' and 16' is positioned a fibrillator roller 17' over which the film tape 4' is passed. Penetration of the film by the fibrillator roller 17' can be adjusted manually so as to give a film which is not actually fibrillated in the sense of being split up into separate fibrils, but which remains coherent and may be caused to fibrillate by slight abrasion. This incipiently fibrillatable film is then collected on a wind-up roller 19'.

Apparatus such as that illustrated schematically in FIG. 1B is also commercially available. One example of such apparatus is the Mark 1 Lab-Line Laboratory Extruder (Plasticisers Engineering Ltd., Drighlington, Bradford).

In the Lab-Line machine, the extruder unit is provided with a nitrided steel extruder screw 22 mm in diameter, with a length:diameter ratio of 21:1 and a compression ratio of 4:1. It is powered by a ½hp DC variable-speed motor flexibly coupled to a worm gear box. The extruder barrel is heated by three independently-controlled electric resistance band heaters. The two chill rollers are of polished hard chrome-plated steel, driven by a ½hp DC variable-speed motor through a worm reduction unit, and are water-cooled.

The draw rollers are also of hard chrome-plated polished steel, and are induction-heated. Surface speed can be varied from 0 to 85 meters per minute.

The wind-up roller is driven by a torque motor, giving accurate control of take-up tension.

The production of dental tapes according to the present invention will now be further illustrated by means of the following Examples.

EXAMPLE 1

An Aspin Sacragrove REF machine was used to produce a 10 inch (25.4 cm) wide film by the cast/chill process. The polymer used was a blend of 89% Solvay polypropylene Eltex 607 (MFI 9), 1% white Masterbatch and 10% polyethylene. Embossing was conducted at a temperature of 90° C. and various embossing pressures and draw ratios. The results obtained are set out in Table 1, which also gives the results of a tensile strength test and a frayability test. The frayability test gives a measure of the likely effect on the tape of catching on overhangs or sharp edges of amalgam or composite fillings.

The tensile strength test was carried out by using direct pull of an Instron testing machine on one tape of the product under examination.

Frayability was tested by means of a fray rig which is mountable on the Instron testing machine. The fray rig provides a pair of opposing hard steel points, the spacing of which is finely adjustable. The tape to be tested is passed through the carefully monitored gap between the points of the rig, thus causing abrasion to the tape. The drop in tensile strength was recorded, or the number of rubs required to cause the tape to break was noted.

It was found that tape produced by the REF process described above was incipiently fibrillatable and suitable for use as a dental tape.

TABLE 1

| | EXPERIMENTAL PARAMETERS | | | TEST RESULTS | | | |
|---|---|---|---|---|---|---|---|
| Sample No. | No. of grooves per cm | Embossing press kgs per sq. cm. | Draw Ratio | Tensile Strength in Kgs (Avg of 6) | Thickness in mm (Avg of 4) | Width of tape in mms | No. of rubs to break (Avg of 5) |
| 1 | 8.0 | 60 | 8:1 | 2.9 | 0.18 | 1.5 | 5.6 |
| 2 | 8.0 | 60 | 7:1 | 3.0 | 0.08 | 1.5 | 4.6 |
| 3 | 6.4 | 80 | 8:1 | — | — | — | — |
| 4 | 6.4 | 60 | 9:1 | — | — | — | — |
| 5 | 6.4 | 40 | 9:1 | 2.9 | 0.08 | 1.5 | 4.8 |

EXAMPLE 2

Polypropylene tapes were produced from two commercially available grades of polypropylene using the Mark 1 Lab-Line machine described above. The extrusion conditions of the Lab-Line machine were maintained as follows:

Screw speed: 41 r.p.m.
Barrel zone 1: 275° C.
Barrel zone 2: 245° C.
Die temperature: 240° C.
Haul-off temperature: 115° C.

It was determined that at draw ratios in excess of 8:1 neither polymer could be satisfactorily extruded and fibrillated. The gentlest fibrillation at the higher draw ratios caused film breakage. However, at a draw ratio of 8:1 or less, films could be produced which were incipiently fibrillatable, and which were suitable for use as dental tape as assessed by the tensile strength test and the frayability test. The results of performing these tests on a number of polypropylene tapes produced at different operating conditions are set out in Table 2.

TABLE 2

| Sample No. | Draw Ratio | Fibrillator Speed (rpm) | Thickness of tape (mm) | Tensile Strength (Kg) | No. of Rubs to break |
|---|---|---|---|---|---|
| GSF1B ICI | | | | | |
| 1 | 8:1 | 165 | 0.058 | 3.77 | 10 |
| 2 | 6:1 | 150 | 0.065 | 3.75 | 15 |
| 3 | 5:1 | 165 | 0.06 | 4.90 | 22 |

TABLE 2-continued

| Sample No. | Draw Ratio | Fibrillator Speed (rpm) | Thickness of tape (mm) | Tensile Strength (Kg) | No. of Rubs to break |
|---|---|---|---|---|---|
| 4 Shell Homopolymer HY0100 | 6:1 | 165 | 0.075 | 4.72 | 17 |
| 5 | 6:1 | 210 | 0.13 | 3.20 | 11 |
| 6 | 6:1 | 180 | 0.07 | 4.62 | 11 |
| 7 | 6:1 | 150 | 0.072 | 5.0 | 15 |
| 8 | 8:1 | 150 | 0.06 | 3.4 | 13 |
| 9 | 8:1 | 180 | 0.06 | 4.43 | 10 |
| 10 | 5:1 | 240 | 0.09 | 3.97 | 10 |
| 11 | 5:1 | 210 | 0.075 | 4.21 | 19 |
| 12 | 5:1 | 180 | 0.075 | 4.2 | 17 |
| 13 | 8:1 | 150 | 0.04 | 3.43 | 8 |
| 14 | 8:1 | 210 | 0.042 | 3.43 | 9 |
| 15 | 8:1 | 210* | 0.045 | 3.47 | 9 |

*For this experiment the position of the fibrillator was moved inward so that the needles gave a maximum degree of penetration.

EXAMPLE 3

Dental tape was also produced from polyethylene, using Montedison Moplen 20. The Lab-Line extruder was run at the following settings:

Extruder speed: 30 r.p.m.
Barrel zone 1: 260° C.
Barrel zone 2: 280° C.
Haul-off temperature: 105° C.

Incipiently fibrillatable tape was produced which was suitable for use as dental tape. It was found that polyethylene produces a thinner film than does polypropylene, but the film does not fibrillate as well as a polypropylene film. Nine experimental tapes were produced, the results being set out in Table 3.

TABLE 3

| Sample | Draw Ratio | Fibrillator Speed (rpm) | Thickness of Tape (mm) | Tensile Strength (Kg) | No. of Rubs to break |
|---|---|---|---|---|---|
| A | 7.5:1 | 300 | 0.032 | 4.4 | 7 |
| B | 7.5:1 | 150 | 0.035 | 4.4 | 8 |
| C | 7.5:1 | 225 | 0.03 | 4.6 | 7.5 |
| E | 7.5:1 | 270 | 0.03 | 4.7 | 7 |
| G | 10:1 | 300 | 0.027 | 3.9 | 5.5 |
| I | 10:1 | 420 | 0.041 | 3.5 | 7 |
| J | 9:1 | 420 | 0.03 | 4.3 | 7 |

TABLE 3-continued

| Sample | Draw Ratio | Fibrillator Speed (rpm) | Thickness of Tape (mm) | Tensile Strength (Kg) | No. of Rubs to break |
|---|---|---|---|---|---|
| K | 9:1 | 330 | 0.028 | 4.5 | 6 |
| N | 9:1 | 360 | 0.031 | 5.2 | 7 |

The incipiently fibrillatable films produced as described above are cut into suitable lengths for dispensing from a handheld container. The tape may, for example, be wound on a rotatable reel housed within the dispenser. A dispenser of this type is illustrated in FIG. 2.

Referring to FIG. 2, a dental tape dispenser comprises a body portion 31 and a lid 33 connected to the body portion 31 by means of an integral hinge. Rotatably mounted within the body portion 31 is a reel 35 around which is wound dental tape 37. The dental tape is fed out of the body portion 31 through a dispensing aperture 39, which aperture is covered by the lid 33 when in the closed position. The body portion is also provided at its upper end with a cutting device 41, in the form of a sharp-edged metal tooth.

If desired, the dental tape of the present invention may be delivered from the dispenser as flavoured tape, e.g. by including a reservoir of flavouring agent in the dispenser. A fluoride may be included in the reservoir and/or tape, as may abrasive materials, and anti-plaque and/or remineralising chemicals.

Further, the dental tape of the present invention may be coloured as by including a pigment in the plastics master-batch.

The production of a dental tape of the present invention is much less complicated than the production of conventional dental floss which involves twisting, doubling and waxing steps. Moreover, the dental tape of the present invention preferably does not involve the use of wax, so that the deposition of wax on the teeth is avoided. If desired however, the tape may be waxed, but preferably with a saliva-soluble wax.

I claim:

1. A dental tape for use in the removal of plaque from teeth, said tape being constituted by a length of incipiently fibrillatable plastics film formed from a polymer selected from the group consisting of polyolefins, polyamides and polyesters and containing at least one additive selected from the group consisting of fluorides, abrasives, anti-plaque agents, remineralizing agents and flavoring agents.

2. A dental tape according to claim 1 wherein the plastics film is a polypropylene film.

* * * * *